United States Patent [19]
Wallace et al.

[11] Patent Number: 5,989,580
[45] Date of Patent: *Nov. 23, 1999

[54] METHODS FOR STERILIZING FEMALE MAMMALS

[75] Inventors: George Wallace, Coto De Caza; Scott Evans, Santa Ana, both of Calif.; Richard J. Greff, St. Petersburg, Fla.

[73] Assignee: Micro Therapeutics, Inc., Irvine, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/763,724

[22] Filed: Dec. 11, 1996

[51] Int. Cl.⁶ .......................... A61M 31/00; A61M 9/08; A61M 31/74; A61M 31/78
[52] U.S. Cl. .................. 424/433; 514/843; 523/105; 523/113; 604/55; 604/25; 128/831
[58] Field of Search .................................. 424/426, 433; 514/843; 523/105, 113; 604/55, 28; 128/831

[56] References Cited

U.S. PATENT DOCUMENTS

| | | |
|---|---|---|
| 3,527,224 | 9/1970 | Rabinowitz et al. . |
| 3,591,676 | 7/1971 | Hawkins et al. . |
| 4,160,446 | 7/1979 | Barrington . |
| 4,210,529 | 7/1980 | Petersen . |
| 4,359,454 | 11/1982 | Hoffman . |
| 4,432,967 | 2/1984 | Szymanski . |
| 4,631,188 | 12/1986 | Stoy et al. . |
| 4,713,235 | 12/1987 | Krall . |
| 5,393,528 | 2/1995 | Staab . |
| 5,469,867 | 11/1995 | Schmitt . |
| 5,488,075 | 1/1996 | Guha . |
| 5,575,815 | 11/1996 | Slepian et al. . |
| 5,580,568 | 12/1996 | Greff et al. . |
| 5,599,552 | 2/1997 | Dunn et al. . |
| 5,667,767 | 9/1997 | Greff et al. . |
| 5,702,361 | 12/1997 | Evans et al. . |

OTHER PUBLICATIONS

Mandai, et al., "Direct Thrombosis of Aneurysms with Cellulose Acetate Polymer",*J. Neurosurg.*, 77:497–500 (1992).
Abstract, Koul, et al., Dose–Dependent Relationship of Polymeric Hydrogels on Motility and Vitality of Human Spermatozoa In–Vitro, *Journal of Materials Science–Materials in Medicine*, 6(4): 192–196 (1995).
Chvapil, et al., "Occlusion of the Vas Deferens in Dogs with a Biocompatible Hydrogel Solution," *J. Reproductive Med.*, 35 (9):905–910 (1990).
Goldsmith, et al., "Transcutaneous Procedures for Male Sterilization," *Adv. Contracept.*, 1:355–361 (1985).
Guha, et al., "Contraception in Male Monkeys by Intra–Vas Deferens Injection of A pH Lowering Polymer", *Contraception*, 32 (1):109–118 (1985).
Guha, et al., "Time–Controlled Injectable Occlusion of the Vas Deferens," *Contraception*, 41(3):323–331 (1990).
Guha, et al. "Phase I Clinical Trial of an Injectable contraceptive for the Male", *Contraception*, 48:367–375 (1993).
Misro, et al., "Injectable Non–Occlusive Chemical Contraception in the Male–I", *Contraception*, 20(5):467–473 (1979).
Sethi, et al., "Histological Changes in the Vas Deferens of Rats After Injection of a New Male Antifertility Agent 'SMA' and Its Reversibility," *Contraception*, 41(3):333–339 (1990).
Sethi, et al., "Safety Evaluation of a Male Injectable Antifertility Agent, Styrene Maleic Anhydride, in Rats," *Contraception*, 39(2):217–227 (1989).
Sethi, et al., "Teratological Evaluation of an Injectable Male Antifertility Agent, Styrene Maleic Anhydride, in Rats", *Int. J. Fertil.*, 37:183–187 (1992).
Sethi, et al., Preclinical Toxicity Study of a Male Injectable Antifertility Agent ( Styrene Maleic Anhydride) in Rhesus Monkeys, Macaca Mulatta, *J. Med. Primatol.*, 20(2):89–93 (1991).
Singh, et al., "Novel Mode of Contraception Using Polymeric Hydrogels. I", *Journal of Biomedical Materials Research*, 16:3–9 (1982).
Verma, et al., "Histology of the Rate Vas Deferens After Injection of a Non–Occlusive Chemical Contraceptive", *J. Reprod. Fert.*, 63:539–542 (1981).
Zhao Sheng–cai, "Vas Deferens Occlusion by Percutaneous Injection of Polyurethane Elastomer Plugs: Clinical Experience and Reversibility," *Contraception*, 41(5):453–459 (1990).
Rakel, *Textbook of Family Practice* , 5th Ed., pp. 726, W.B. Saunders, Philadelphia, PA (1995).
Cunningham, Williams Obstetrics, Chapter 62, Surgical Contraception, pp. 1353–1359, Appleton & Lange, Norwalk, CT (1993).
Dewitt, "Surgery of the Male Genital Tract", in *Family Medicine Principles and Practice*, 4th Edition, Taylor, Editor, pp. 778–780 (1994).
Kinugasa, et al., "Direct Thrombosis of Aneurysms with Cellulose Acetate Polymer", *J. Neurosurg.*, 77:501–507 (1992).
Kinugasa, et al., "Early Treatment of Subarachnoid Hemorrhage After Preventing Rerupture of an Aneurysm", *J. Neurosurg.*, 83:34–41 (1995).
Kinugasa, et al., "Prophylactic Thrombosis to Prevent New Bleeding and to Delay Aneurysm Surgery", *Neurosurg.*, 36:661 (1995).
Taki, et al., "Selection and Combination of Various Endovascular Techniques in the Treatment of Giant Aneurysms", *J. Neurosurg.*, 77:37–42 (1992).
Park, et al., "New Polymers of Therapeutic Embolization", Poster #47, Meeting of the Radiological Society of North America (1993).

*Primary Examiner*—Edward J. Webman
*Attorney, Agent, or Firm*—Burns, Doane, Swecker & Mathis, LLP

[57] ABSTRACT

Disclosed are methods for sterilizing a female mammal wherein a composition comprising a biocompatible polymer and a biocompatible solvent is delivered to the fallopian tube of the female mammal.

24 Claims, No Drawings

METHODS FOR STERILIZING FEMALE MAMMALS

BACKGROUND OF THE INVENTION

Field of the Invention

This invention is directed to methods for sterilizing female mammals generally and female humans in particular.

In the methods of this invention, a composition comprising a biocompatible polymer, a biocompatible solvent and a contrast agent is delivered to the fallopian tube of the female mammal. The biocompatible polymer is selected to be soluble in the biocompatible solvent, but insoluble in the aqueous fluid of the fallopian tube. The biocompatible solvent is miscible or soluble in this aqueous fluid and, upon contact with this fluid, the biocompatible solvent quickly diffuses away whereupon the biocompatible polymer precipitates to form an occlusion in the fallopian tube which blocks the passage of eggs from the ovary.

A significant advantage of the methods of this invention is that the sterilization can be reversed merely by dissolving the biocompatible polymer forming the occlusion with the biocompatible solvent.

REFERENCES

The following publications are cited in this application as superscript numbers:

1. Rakel, *Textbook of Family Practice*, 5th Ed., pp. 726, W. B. Saunders, Philadelphia, Pa. (1995).
2. Cunningham, *Williams Obstetrics*, Chapter 62, *Surgical Contraception*, pp. 1353–1359, Appleton & Lange, Norwalk, Conn. (1993),
3. Dewitt, "Surgery of the Male Genital Tract", in *Family Medicine Principles and Practice*, 4th Edition, Taylor, Editor, pp. 778–780 (1994).
4. Stoy, et al., U.S. Pat. No. 4,631,188, for "Injectable Physiologically-Acceptable Polymeric Composition", issued Dec. 23, 1986.
5. Rabinowitz, et al., U.S. Pat. No. 3,527,224, for "Method of Surgically Bonding Tissue Together", issued Sep. 8, 1970.
6. Hawkins, et al., U.S. Pat. No. 3,591,676, for "Surgical Adhesive Compositions", issued Jul. 6, 1971.
7. Kinugasa, et al., "Direct Thrombosis of Aneurysms with Cellulose Acetate Polymer", *J. Neurosurg.*, 77:501–507 (1992).
8. Greff, et al., U.S. Pat. No. 5,667,767 for "Novel Compositions for Use in Embolizing Blood Vessels", issued on Sep. 16, 1997.
9. Greff, et al., U.S. Pat. No. 5,580,568 for "Cellulose Diacetate Compositions for Use in Embolizing Blood Vessels", issued Dec. 3, 1996.
10. Kinugasa, et al., "Early Treatment of Subarachnoid Hemorrhage After Preventing Rerupture of an Aneurysm", *J. Neurosurg.*, 83:34–41 (1995).
11. Kinugasa, et al., "Prophylactic Thrombosis to Prevent New Bleeding and to Delay Aneurysm Surgery", *Neurosurg.*, 36:661 (1995).
12. Taki, et al., "Selection and Combination of Various Endovascular Techniques in the Treatment of Giant Aneurysms", *J. Neurosurg.*, 77:37–42 (1992). Park, et al., "New Polymers for Therapeutic Embolization", Poster #47, Meeting of the Radiological Society of North America (1993).

All of the above references are herein incorporated by reference in their entirety to the same extent as if each individual reference was specifically and individually indicated to be incorporated herein by reference in its entirety.

STATE OF THE ART

Normal surgical contraceptive methods include both vasectomy (males) and tubal ligation (females).[1,2,3] For females, tubal ligation has been recognized as one of the safest, simplest, and most effective forms of sterilization with mortality rates as low as 3 per 100,000[2]. As normally practiced, tubal ligation involves a skin incision and subsequent inactivation of the fallopian tubes. Procedures recognized in the art of tubal ligation include the Irving procedure, the Pomeroy procedure, the Madlener procedure, the Parkland procedure and the Kroener fimbriectomy procedure each of which is discussed and illustrated by Cunningham[2].

Notwithstanding its safety and efficacy, tubal ligation has not gained wide acceptance as a form of female contraception partially because it is a surgical procedure requiring a sterile environment and has possible complications including hemorrhage, infection, anesthetic complications, scarring, formation of adhesions, and the like.[2]

Another drawback of tubal ligation is a lack of reversibility. While some female mammals have successfully reproduced after having surgical sterilization, the success rate is not high enough to make the procedure more appealing as a form of female contraception and the procedure is generally construed as irreversible.

In view of the above drawbacks, attempts have been made to develop a non-surgical and reversible method of female sterilization. One such attempt involves the injection of a polymeric hydrogel solution in a suitable solvent such as DMSO into the fallopian tubes.[4] Upon injection into the fallopian tubes, the polymeric composition slowly coagulates into a spongy polymer structure which takes up water to from a hydrogel composition.

However, the procedures described in Stoy[4] are hampered by the fact that the injection procedure is difficult to monitor and it is also difficult to determine whether the procedure, when completed, has been successful. Moreover, Stoy's hydrogels are reported as causing osmotic shock to neighboring tissue and the coagulation process is rather slow resulting in a sponganeous polymer forming in situ. This slow coagulation process could lend itself to migration of at least some of the polymer from the intended site of application prior to formation of the sponganeous polymer with the concomittant possibility that the sterilization process will be unsuccessful.

In view of the above drawbacks, a need continues to exist in the art for an easy, reliable, and dependable method of sterilizing female mammals.

This invention is directed to the discovery that the efficacy of female sterilization by placement of a polymer composition dissolved in a solvent can be enhanced by further delivery of a contrast agent as described below into the fallopian tubes. The contract agent permits monitoring of the injection while it is taking place to ensure that the sterilization procedure is being carried out properly. The methods described herein can also be reversed quickly and reliably to restore the female's reproductive capacity. Moreover, the use of a water insoluble contrast agent in the sterilization procedure has the added advantage of providing a facile means to locate the polymeric blockage in the fallopian tubes potentially years after the polymer has been placed there.

SUMMARY OF THE INVENTION

This invention is directed to the discovery that unexpected and surprising results are achieved when female mammals are sterilized with a composition comprising a biocompatible polymer, a biocompatible solvent, and a contrast agent. In particular, deficiencies associated with each of the prior art procedures are either reduced or eliminated by the invention. Such deficiencies include, for example, problems associated with a skin incision and problems associated with readily reversing the sterilization process.

Accordingly, this invention is directed to a method for sterilizing a female mammal, which method comprises delivering a composition comprising a biocompatible polymer, a biocompatible solvent and a contrast agent into the fallopian tube of the female mammal
  wherein said delivery is conducted under conditions such that a polymer precipitate forms in situ in the fallopian tube thereby sterilizing the female mammal.

In the composition, the biocompatible polymer is preferably an ethylene vinyl alcohol copolymer or a cellulose acetate polymer. The biocompatible solvent is preferably dimethylsulfoxide.

In another embodiment, the biocompatible polymer is replaced with a biocompatible prepolymer. In this embodiment, this invention is directed to a method for sterilizing a female mammal, which method comprises delivering a composition comprising a biocompatible prepolymer to the fallopian tube of the female mammal
  wherein said delivery is conducted under conditions such that said prepolymer polymerizes in situ in the fallopian tube thereby sterilizing the female mammal.

In the composition, the prepolymer is preferably selected from the group consisting of cyanoacrylates and urethane prepolymers.

In one optional embodiment, the composition further comprises a biocompatible solvent which is preferably selected from the group consisting of dimethylsulfoxide, ethanol, and acetone.

In another aspect, this invention is directed to a reversible method for sterilizing a female mammal, which method comprises delivering a composition comprising a biocompatible polymer, a contrast agent and a first biocompatible solvent to the fallopian tube of the female mammal
  wherein said delivery is conducted under conditions such that a polymer precipitate forms in situ in the fallopian tube thereby sterilizing the female mammal and
  reversing said sterilization by contacting said polymer precipitate formed in the fallopian tube with a second biocompatible solvent under conditions such that said polymer precipitate dissolves in said second biocompatible solvent thereby reversing said sterilization of the female mammal.

In a particularly preferred embodiment, the contrast agent is a water insoluble contrast agent which, upon precipitation of the polymer in situ, will form part of the precipitate. Upon reversing the sterilization process, the contrast agent retained in the polymeric composition is employed to identify the location of the polymeric blockage in the fallopian tubes.

In one embodiment, the first biocompatible solvent and the second biocompatible solvent are the same.

In the composition, the biocompatible polymer is preferably an ethylene vinyl alcohol copolymer or a cellulose acetate polymer. The first and second biocompatible solvents are preferably dimethylsulfoxide.

DETAILED DESCRIPTION OF THE INVENTION

This invention is directed to methods for sterilizing female mammals, which methods comprise delivering a composition comprising a biocompatible polymer, a biocompatible solvent, and a contrast agent to the fallopian tube of the female mammal.

Prior to discussing this invention in further detail, the following terms will first be defined:

The term "sterilizing" refers to a process for making a person or an animal unable to produce offspring. In the context of this invention, sterilization is carried out by delivering a material into the fallopian tube of the female mammal. The material then fills or plugs the fallopian tube so that eggs cease to pass therethrough.

The term "biocompatible polymer" refers to polymers which, in the amounts employed, are non-toxic, chemically inert, and substantially non-immunogenic when used internally in the female mammal and which are substantially insoluble in the fluid of the fallopian tube. The chemically inert polymers do not appreciably absorb water upon contact with the fluid of the fallopian tubes and typically will have an equilibrium water content of less than about 25% water and preferably less than about 15% water. Suitable biocompatible polymers include, by way of example, cellulose acetates[7,10,11] (including cellulose diacetate[9]), ethylene vinyl alcohol copolymers[8,12], polyalkyl($C_1$–$C_6$) acrylates, polyalkyl alkacrylates wherein the alkyl and the alk groups contain no more than 6 carbon atoms, polyacrylonitrile and the like. Other polymers suitable for use herein include those disclosed in U.S. patent application Ser. No. 08/655,822 filed concurrently herewith as Attorney Docket No. 018413-010 and entitled "Novel Compositions for Use in Embolizing Blood Vessels" which application is incorporated herein by reference in its entirety. Further examples of biocompatible polymers are provided by Park, et al.[13] Preferably, the biocompatible polymer is also non-inflammatory when employed in vivo.

The particular biocompatible polymer employed is not critical and is selected relative to the viscosity of the resulting polymer solution, the solubility of the biocompatible polymer in the biocompatible solvent, and the like. Such factors are well within the skill of the artisan.

Preferred biocompatible polymers include cellulose diacetate and ethylene vinyl alcohol copolymer. Cellulose diacetate polymers are either commercially available or can be prepared by art-recognized procedures. In a preferred embodiment, the number average molecular weight, as determined by gel permeation chromatography, of the cellulose diacetate composition is from about 25,000 to about 100,000; more preferably from about 50,000 to about 75,000; and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate, and the like.

Ethylene vinyl alcohol copolymers are either commercially available or can be prepared by art-recognized procedures. Preferably, the ethylene vinyl alcohol copolymer composition is selected such that a solution of 6 weight percent of the ethylene vinyl alcohol copolymer, 35 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity of the composition as compared to higher molecular weight copolymers. Accordingly, adjustment of the viscosity of the composition as necessary for catheter or needle delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative solubility of the composition in the biocompatible solvent as well as the rate of precipitation of the copolymer in an aqueous solution (e.g., blood). In a particularly preferred embodiment, the copolymers employed herein comprise a mole percent of ethylene of from about 25 to about 60 and a mole percent of vinyl alcohol of from about 40 to about 75. More preferably, these copolymers comprise from about 40 to about 60 mole percent of vinyl alcohol and from about 60 to 40 mole percent of ethylene. These compositions provide for requisite precipitation rates suitable for use in sterilizing female mammals.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a particle size of about 10 μm or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the female mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the fallopian tube fluid, e.g., less than about 5%. Preferably, the biocompatible solvent is dimethylsulfoxide (DMSO).

The term "biocompatible prepolymer" refers to materials which polymerize in situ to form a polymer and which, in the amounts employed, are non-toxic, chemically inert, and substantially non-immunogenic when used internally in the female mammal and which are substantially insoluble in the fallopian tube fluid. Suitable biocompatible prepolymers include, by way of example, cyanoacrylates[5,6], urethane prepolymers, and the like. The prepolymer can either be a monomer or a reactive oligomer although reactive oligomers are preferred[5]. Preferably, the biocompatible prepolymer is also non-inflammatory when employed in vivo.

COMPOSITIONS

The polymer or prepolymer employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer composition based on the total weight of the polymer composition, including contrast agent and solvent, and more preferably from about 4 to about 5.2 weight percent. If necessary, gentle heating and stirring can be used to effect dissolution of the biocompatible polymer into the biocompatible solvent, e.g. 12 hours at 50° C.

Sufficient amounts of the contrast agent are then added to the solution to achieve the effective concentration for the complete polymer composition. Preferably, the polymer composition will comprise from about 10 to about 40 weight percent of the contrast agent and more preferably from about 20 to about 40 weight percent and even more preferably 35 weight percent based on the total weight of the composition including the biocompatible polymer and biocompatible solvent. When the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g. an average size of about 2 μm).

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition may be heat sterilized and then stored preferably in sealed amber bottles or vials until needed.

Prepolymer compositions can be prepared by adding sufficient amounts of the contrast agent to the prepolymer to achieve the effective concentration for the complete polymer composition. Preferably, the prepolymer composition will comprise from about 10 to about 40 weight percent of the contrast agent and more preferably from about 20 to about 40 weight percent and even more preferably 35 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm). In one preferred embodiment, the particle size of a water insoluble contrast agent is prepared, for example, by fractionation. In such an embodiment, a water insoluble contrast agent such as tantalum having a particle size of less than about 20 micron is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under a microscope. The process is optionally repeated until a desired particle size is reached.

When the prepolymer is liquid (as in the case of polyurethanes), the use of a biocompatible solvent is not absolutely necessary but may be preferred to provide for an appropriate viscosity, etc. in the composition. Preferably, when employed, the biocompatible solvent will comprise from about 50 to about 90 weight percent of the biocompatible prepolymer composition based on the total weight of the prepolymer composition and more preferably from about 60 to about 80 weight percent.

In a particularly preferred embodiment, the prepolymer is cyanoacrylate which is preferably employed in the absence of a biocompatible solvent. When so employed, the cyanoacrylate prepolymer is selected to have a viscosity of from about 5 to about 100 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

METHODS

The compositions described above are then employed in methods for sterilizing female mammals. In these methods, the composition is introduced to the fallopian tube via conventional laproscopic, catheter, or needle technology.

Upon discharge of the composition into the fallopian tube, the biocompatible solvent dissipates into the fallopian tube fluid resulting in the precipitation of the biocompatible polymer. The precipitate forms in the fallopian tube which acts as a plug to stop the flow of eggs from the ovary to the uterus.

The particular amount of polymer composition employed is dictated by the diameter of the fallopian tube, the concentration of polymer in the composition, the rate of precipitation (solids formation) of the polymer, etc. Such factors are well within the skill of the artisan. For example, the rate of precipitation can be controlled by changing the overall hydrophobicity/hydrophilicity of the polymer with faster precipitation rates being achieved by a more hydrophobic polymer composition.

One particularly preferred method for delivering the composition to the fallopian tube is via a small diameter medical catheter. The particular catheter employed is not critical provided that polymeric catheter components are compatible with the polymeric composition (i.e., the catheter components will not readily degrade in the polymer composition and none of the components of the polymer compositions will readily degrade in the presence of the catheter components). In this regard, it is preferred to use polyethylene in the catheter components because of its inertness in the presence of the polymeric composition described herein. Other materials compatible with the composition can be readily determined by the skilled artisan and include, for example, other polyolefins, fluoropolymers (e.g., Teflon), silicone, etc.

When delivered by catheter, the injection rate of the polymer composition dictates, in part, the form of the precipitate in the fallopian tube. Specifically, low injection rates of approximately 0.05 to 0.3 cc/minute will provide for a precipitate in the form of a kernel or nodule which is particularly beneficial because the precipitate forms primarily at the point of injection.

When introduced, the biocompatible solvent rapidly diffuses into the fluid present in the fallopian tube leaving a solid precipitate. The precipitate is a combination of the biocompatible polymer and the contrast agent. Without being limited to any theory, it is believed that initially, a soft gel to spongy solid precipitate forms upon contact with the fallopian tube fluid. This precipitate then restricts the migration of eggs from the ovary to the uterus thereby sterilizing the female mammal.

The methods described herein can also employ a biocompatible prepolymer such as a urethane or cyanoacrylate prepolymer in place of or in conjunction with the polymer composition described above. When the prepolymer is liquid (as in the case of cyanoacrylates), the use of a biocompatible solvent is not absolutely necessary but may be preferred to provide for an appropriate viscosity, etc. in the composition. Upon injection into the fallopian tube, the prepolymer will polymerize in situ upon contact with the fallopian tube fluid and form a solid polymer therein. The solid polymer blocks the passage of eggs from the ovary to the uterus of the female mammal thereby sterilizing the female mammal.

The methods of this invention facilitate female sterilization because the presence of the contrast agent in the composition permits monitoring of the delivery of the biocompatible polymer while it is taking place. In this way, one can ensure that the biocompatible polymer is being delivered to the fallopian tubes as well as determine whether the size of the polymer precipitate thus-formed will be sufficient to block the passage of eggs.

In another aspect of this invention, the above-described sterilization procedure can be easily and reliably reversed. In such a case, the same procedures as sterilization are carried out except without the use of a biocompatible polymer and contrast agent. Specifically, a composition comprising a biocompatible solvent is delivered to the fallopian tube at or near the location of the polymer precipitate previously deposited therein. The biocompatible solvent acts to dissolve and flush out the polymer precipitate. The fallopian tube is thereby restored to its previous condition and eggs can again pass therethrough.

Without being limited to any theory, the methods of this invention address the prior art problems recited above because the polymer precipitate formed in the fallopian tube can be dissolved and flush out with a biocompatible solvent after a period of time. Thus, the reproductive capacity of the female mammal may be restored safely and effectively. Additionally, if the polymer composition is delivered via conventional needle technology, the necessity of a skin incision can be avoided.

UTILITY

The methods described herein are useful in sterilizing female mammals which, in turn, can be used to prevent/control reproduction. Accordingly, these methods find use in human and other mammalian subjects requiring sterilization.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

cc=cubic centimeter

DMSO=dimethylsulfoxide

EVOH=ethylene vinyl alcohol copolymer mm=millimeter

μm=micron

In the following examples, Examples 1–2 illustrate the preparation of polymer compositions useful in the methods described herein which polymer compositions comprise cellulose acetate and EVOH. Examples 3 and 4 illustrate how such polymer compositions could be used in the methods of this invention.

EXAMPLE 1

A cellulose diacetate polymer composition was prepared by dissolving cellulose acetate (39.7 weight percent acetyl content) into DMSO to provide for an 6.8 weight percent concentration of the polymer in DMSO. To this solution was added either tantalum (10 weight percent, available from Leico Industries, New York, N.Y. USA. 99.95% purity, less than 43 μm in size) as a water insoluble contrast agent or metrizamide (38.5 weight percent, available from Aldrich Chemical Company, Milwaukee, Wis., USA) as a water soluble contrast agent.

In the tantalum composition, tantalum settling can result from prolonged standing. Sonification may help but thorough mixing prior to use is required.

In the Example above, tantalum powder can also be obtained from Aldrich Chemical Company, Milwaukee, Wis., USA.

Preferably the composition comprises from about 25 to about 35 weight percent tantalum.

EXAMPLE 2

An EVOH polymer composition was prepared by dissolving EVOH (44 mole percent ethylene) into DMSO to provide for an 6.8 weight percent concentration of the copolymer in DMSO. In order to facilitate dissolution, the system can be heated to 50° C. overnight.

To this solution was added either tantalum (10 weight percent, available from Leico Industries, New York, N.Y., USA. 99.95% purity, less than 43 μm in size) as a water insoluble contrast agent or metrizamide (38.5 weight percent, available from Aldrich Chemical Company, Milwaukee, Wis., USA) as a water soluble contrast agent.

In the tantalum composition, tantalum settling can result from prolonged standing. Sonification may help but thorough mixing prior to use is required.

Preferably the composition comprises from about 25 to about 25 weight percent tantalum.

EXAMPLE 3

The purpose of this example is to illustrate how an in vivo application of the methods of this invention in the sterilization of a female mammal could be accomplished.

In this example, a 40 pound female dog is prepared for sterilization using a composition comprising 5.8 weight percent EVOH polymer (containing 48 weight percent ethylene). 20 weight percent tantalum in DMSO. The composition is loaded into a syringe having a long needle. The needle is then inserted into the lower abdominal area of the subject. The process of the needle and the location of the fallopian tube can be monitored by conventional fluoroscopic techniques. Once the needle punctures the fallopian tube, the EVOH polymer composition (0.3 cc) is then delivered from the syringe to the fallopian tube. The delivery is easily visualized with fluoroscopy due to the presence of a contrast agent in the polymer composition. After delivery, the DMSO in the EVOH composition rapidly diffuses and the EVOH precipitates in the fallopian tube resulting in blockage of the tube. After about 5 minutes, the polymer is fully precipitated and the needle is removed from fallopian tube.

The same procedure is repeated with the other fallopian tube of the female subject.

EXAMPLE 4

The purpose of this example is to illustrate how an in vivo application of the methods of this invention in reversing the sterilization of a female mammal could be accomplished.

In this example, the procedures of Example 3 are followed except that the polymer composition is replaced with the biocompatible solvent. Approximately 0.3 to 0.5 cc of DMSO is injected into the occluded fallopian tube over a period of 1 to 2 minutes to dissolve the previously deposited polymer precipitate which is removed by pulling back on the syringe. The procedure is repeated twice more. The dissolving and flushing of the precipitate is easily visualized with fluoroscopy due to the presence of a contrast agent in the polymer. After about 10 minutes, the polymer is fully dissolved and evacuated, and the syringe needle is removed from the fallopian tube.

EXAMPLE 5

The purpose of this example is to illustrate ex vivo reversibility of the process. Specifically, six (6) segments of coronary arteries were excised from fresh lamb hearts, obtained from a local meat store that day. The arteries (vessels) were approximately 6 cm in length and varied in diameter from about 1.5 to about 3.0 mm. Each segment was washed and then flushed with normal saline at room temperature.

The vessel segments were placed in a beaker filled with normal saline and a polymer composition comprising 7 weight percent cellulose acetate polymer (39% acetyl content) and 30 weight percent tantalum in DMSO was injected from a 3 cc syringe into each vessel through a 20 gage needle. Approximately 1 to 3 cm of each vessel was filled with the polymer composition and injection was over a 10 to 15 second period. Attempts to flush the vessel with normal saline showed no flow or total vessel occlusion.

After 15 minutes, a new 3 cc syringe and 20 gage needle filled with DMSO was introduced into the vessel, just proximal to the polymer plug. Gentle injection/aspiration of the DMSO over a 1 minute period yielded a noticeable dissolution of the polymer, with recanalization of the vessel within 2 to 3 minutes. Dissolution of the polymer plug took about 5 minutes. This result was repeated in all vessel segment samples.

It is understood that the same procedures set forth above can be employed with compositions employing liquid prepolymers. However, when so employed, the timing and injection rates will vary depending on the cure rate for the prepolymer. Such factors are within the skill of the artisan.

From the foregoing description, various modifications and changes in the composition and method will occur to those skilled in the art. All such modifications coming within the scope of the appended claims are intended to be included therein.

What is claimed is:

1. A method for sterilizing a female mammal wherein said sterilization is reversible, which method comprises delivering a composition comprising a biocompatible polymer having an equilibrium water content of less than about 15% with the proviso that the biocompatible polymer is not polyacrylonitrile, a radiopaque contrast agent and a biocompatible solvent to the fallopian tubes of the female mammal wherein said delivery is conducted under conditions such that a polymer precipitate forms in situ in the fallopian tubes thereby sterilizing the female mammal.

2. The method according to claim 1 wherein said biocompatible polymer is selected from the group consisting of cellulose acetate polymers, ethylene vinyl alcohol copolymers, and polyacrylates.

3. The method according to claim 2 wherein said biocompatible polymer is a cellulose acetate polymer or an ethylene vinyl alcohol copolymer.

4. The method according to claim 1 wherein said biocompatible solvent is selected from the group consisting of dimethylsulfoxide, ethanol, and acetone.

5. The method according to claim 4 wherein said biocompatible solvent is dimethylsulfoxide.

6. The method according to claim 1 wherein said contrast agent is a water insoluble contrast agent.

7. The method according to claim 6 wherein said water insoluble contrast agent is selected from the group consisting of tantalum, tantalum oxide, tungsten, and barium sulfate.

8. The method according to claim 1 wherein said contrast agent is a water soluble contrast agent.

9. The method according to claim 8 wherein said water soluble contrast agent is metrizamide.

10. The method according to claim 1 wherein said composition is delivered into the fallopian tube via a catheter.

11. The method according to claim 1 wherein said composition is delivered into the fallopian tube via a needle.

12. A reversible method for sterilizing a female mammal, which method comprises delivering a composition comprising a biocompatible polymer having an equilibrium water content of less than about 15% with the proviso that the biocompatible polymer is not polyacrylonitrile, a radiopaque contrast agent and a biocompatible solvent to the fallopian tubes of the female mammal wherein said delivery is conducted under conditions such that a polymer precipitate forms in situ in the fallopian tubes thereby sterilizing the female mammal and further wherein said sterilization is reversed by contacting said polymer precipitate formed in the fallopian tube with a second biocompatible solvent under conditions such that said polymer dissolves in said second biocompatible solvent thereby reversing said sterilization of the female mammal.

13. The method according to claim 12 wherein said biocompatible polymer is selected from the group consisting of cellulose acetate polymers, ethylene vinyl alcohol copolymers and polyacrylates.

14. The method according to claim 13 wherein said biocompatible polymer is a cellulose acetate polymer or an ethylene vinyl alcohol copolymer.

15. The method according to claim 12 wherein said first biocompatible solvent and said second biocompatible solvent are the same.

16. The method according to claim 12 wherein each of said first biocompatible solvent and said second biocompatible solvent is selected from the group consisting of dimethylsulfoxide, ethanol, and acetone.

17. The method according to claim 16 wherein said first biocompatible solvent and said second biocompatible solvent are dimethylsulfoxide.

18. The method according to claim 12 wherein said contrast agent is a water insoluble contrast agent.

19. The method according to claim 18 wherein said water insoluble contrast agent is selected from the group consisting of tantalum, tantalum oxide, tungsten, and barium sulfate.

20. The method according to claim 12 wherein said contrast agent is a water soluble contrast agent.

21. The method according to claim 20 wherein said water soluble contrast agent is metrizamide.

22. The method according to claim 12 wherein said composition is delivered into the fallopian tube via a catheter or a needle.

23. The method according to claim 12 wherein said second biocompatible solvent is delivered into the fallopian tube via a catheter or a needle.

24. The method according to claim 12 wherein said second biocompatible solvent further comprises a contrast agent.

* * * * *